US009585385B2

United States Patent
Ueda et al.

(10) Patent No.: US 9,585,385 B2
(45) Date of Patent: Mar. 7, 2017

(54) COPPER COMPLEX TITANIUM OXIDE DISPERSION LIQUID, COATING AGENT COMPOSITION, AND ANTIBACTERIAL/ANTIVIRAL MEMBER

(71) Applicant: Panasonic Intellectual Property Management Co., Ltd., Osaka (JP)

(72) Inventors: Takeshi Ueda, Osaka (JP); Daigo Yamashina, Osaka (JP); Kensaku Kinugawa, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 14/764,705

(22) PCT Filed: Feb. 26, 2014

(86) PCT No.: PCT/JP2014/000999
§ 371 (c)(1),
(2) Date: Jul. 30, 2015

(87) PCT Pub. No.: WO2014/141600
PCT Pub. Date: Sep. 18, 2014

(65) Prior Publication Data
US 2015/0351386 A1    Dec. 10, 2015

(30) Foreign Application Priority Data

Mar. 13, 2013  (JP) ................................. 2013-050239
Apr. 26, 2013  (JP) ................................. 2013-094288
Dec. 12, 2013  (JP) ................................. 2013-257283

(51) Int. Cl.
| | | |
|---|---|---|
| *A01N 59/20* | (2006.01) | |
| *A01N 59/16* | (2006.01) | |
| *A01N 25/30* | (2006.01) | |
| *A01N 25/04* | (2006.01) | |
| *C09D 5/14* | (2006.01) | |
| *C09D 7/12* | (2006.01) | |
| *C09D 17/00* | (2006.01) | |
| *C09D 201/00* | (2006.01) | |
| *C09D 1/00* | (2006.01) | |
| *C01G 23/00* | (2006.01) | |

(52) U.S. Cl.
CPC ............ *A01N 25/30* (2013.01); *A01N 25/04* (2013.01); *A01N 59/16* (2013.01); *A01N 59/20* (2013.01); *C01G 23/002* (2013.01); *C09D 1/00* (2013.01); *C09D 5/14* (2013.01); *C09D 7/12* (2013.01); *C09D 7/1208* (2013.01); *C09D 17/00* (2013.01); *C09D 201/00* (2013.01); *C01P 2004/04* (2013.01); *C01P 2004/62* (2013.01); *C01P 2004/64* (2013.01)

(58) Field of Classification Search
None
See application file for complete search history.

(56) References Cited

U.S. PATENT DOCUMENTS

| | | | | |
|---|---|---|---|---|
| 4,036,950 A | * | 7/1977 | Baines ................... | A61K 8/416 424/52 |
| 7,645,436 B1 | * | 1/2010 | Ryang ................... | B82Y 30/00 423/299 |
| 8,182,786 B2 | * | 5/2012 | O'Brien ................... | A61K 8/19 423/632 |
| 2004/0065619 A1 | * | 4/2004 | Klabunde ............. | B01D 53/02 210/681 |
| 2006/0060998 A1 | * | 3/2006 | Strouse ................... | B01J 13/00 264/5 |
| 2010/0040655 A1 | * | 2/2010 | Ren ......................... | A01N 25/34 424/402 |
| 2011/0217544 A1 | * | 9/2011 | Young ................ | B29C 37/0032 428/327 |
| 2013/0034472 A1 | * | 2/2013 | Cantrell ............ | B01D 53/9422 422/177 |
| 2013/0281283 A1 | | 10/2013 | Hashimoto et al. | |
| 2015/0351386 A1 | * | 12/2015 | Ueda ........................ | C09D 1/00 523/122 |

FOREIGN PATENT DOCUMENTS

| | | |
|---|---|---|
| CN | 101322939 A | 12/2008 |
| EP | 2 161 316 A1 | 3/2010 |

(Continued)

OTHER PUBLICATIONS

International Search Report for corresponding International Application No. PCT/JP2014/000999 mailed May 20, 2014.
Form PCT/ISA/237 for corresponding International Application No. PCT/JP2014/000999 dated May 20, 2014.

*Primary Examiner* — Peter A Salamon

(74) *Attorney, Agent, or Firm* — Renner, Otto, Boisselle & Sklar, LLP

(57) ABSTRACT

A copper complex titanium oxide dispersion liquid includes: titanium oxide particles; and 0.1 to 20 parts by mass of cuprous oxide particles per 100 parts by mass of the titanium oxide particles. The dispersion liquid further includes: 5 to 100 parts by mass of phosphate ester-based anionic surfactant per 100 parts by mass of the titanium oxide particles and the cuprous oxide particles combined; and 300 to 2000 parts by mass of an organic solvent per 100 parts by mass of the titanium oxide particles and the cuprous oxide particles combined. The titanium oxide particles and the cuprous oxide particles have an average primary particle diameter of 2 nm to 80 nm and have an average secondary particle diameter of 50 nm to 150 nm as measured by dynamic light scattering using cumulant analysis. Moreover, 10 or more parts by mass of the titanium oxide particles are contained in 100 parts by mass of non-volatile matter content of the copper complex titanium oxide dispersion liquid.

5 Claims, No Drawings

(56) References Cited

FOREIGN PATENT DOCUMENTS

| | | |
|---|---|---|
| EP | 2 692 439 A1 | 2/2014 |
| JP | 2003-275601 A | 9/2003 |
| JP | 2005-097400 A | 4/2005 |
| JP | 2007-070299 A | 3/2007 |
| JP | 2008-255101 A | 10/2008 |
| JP | 2011-042642 A | 3/2011 |
| JP | 2013-194181 A | 9/2013 |
| JP | 2013-194182 A | 9/2013 |
| WO | WO 2009/001619 A1 | 12/2008 |
| WO | WO 2012/132716 A1 | 10/2012 |
| WO | WO 2013/002151 A1 | 1/2013 |
| WO | WO 2013/054860 A1 | 4/2013 |

\* cited by examiner

COPPER COMPLEX TITANIUM OXIDE DISPERSION LIQUID, COATING AGENT COMPOSITION, AND ANTIBACTERIAL/ANTIVIRAL MEMBER

TECHNICAL FIELD

The present invention relates to a copper complex titanium oxide dispersion liquid, a coating agent composition, and an antibacterial/antiviral member. To be specific, the present invention relates to a copper complex titanium oxide dispersion liquid and a coating agent composition which provide high antibacterial and antiviral performances and transparency, and relates to an antibacterial/antiviral member including the coating agent composition.

BACKGROUND ART

Various types of antibacterial members have been developed and turned into products to reduce microbes in the environment because of increased consumers' consciousness of hygiene. In general, antibacterial members used for interior members in houses or vehicles contain antibacterial materials such as silver and zinc (for example, refer to Patent Literatures 1 and 2). However, silver and zinc have a problem of costs or biological toxicity.

Accordingly, attempts are being made to use titanium oxide, which is cheap, abundant, and less ecotoxic, as an antibacterial material (for example, refer to Patent Literature 3). Titanium oxide is photocatalytically active, and the antibacterial action using the photocatalytic activity thereof is attracting attention.

Herein, titanium oxide is white powder as often used in pigment of white paint. To use antibacterial members in various applications, some techniques are required to ensure the transparency thereof even when the antibacterial members include titanium oxide. Specifically, titanium oxide needs to be microparticulated using bottom-up synthesis or various dispersion techniques.

CITATION LIST

Patent Literature

Patent Literature 1: Japanese Unexamined Patent Application Publication No. 2008-255101
Patent Literature 2: Japanese Unexamined Patent Application Publication No. 2011-42642
Patent Literature 3: Japanese Unexamined Patent Application Publication No. 2003-275601

SUMMARY OF INVENTION

However, major dispersion liquids of titanium oxide particles currently on the market are aqueous dispersion liquids using charge repulsion between particles. If such aqueous dispersion liquids of titanium oxide are used together with a binder composed of a combination of acrylic urethane and isocyanate, the transparency could be degraded by the effect of water. Moreover, using such a binder with aqueous dispersion liquid of titanium oxide can extremely shorten the working life thereof.

The conventional dispersion liquid of titanium oxide particles has low concentration of titanium oxide. When the concentration of titanium oxide is low, the applied coating becomes thick, and problems such as drips tend to occur. Moreover, the conventional dispersion liquid contains a lot of solvent and therefore requires longer drying time and higher drying temperature. Furthermore, in addition to further increasing the antibacterial performance of the antibacterial materials, it is necessary to provide antiviral performance for the antibacterial members.

The present invention has been made in view of the above-described conventional problems. An object of the present invention is to provide a copper complex titanium oxide dispersion liquid and a coating agent composition which can form a transparent coating film including antibacterial performance increased by increasing the concentration of the antibacterial material and further including antiviral performance. Another object of the present invention is to provide an antibacterial/antiviral member including the coating agent composition.

A copper complex titanium oxide dispersion liquid according to a first aspect of the present invention includes: titanium oxide particles; and 0.1 to 20 parts by mass of cuprous oxide particles per 100 parts by mass of the titanium oxide particles. The dispersion liquid includes: 5 to 100 parts by mass of phosphate ester-based anionic surfactant per 100 parts by mass of the titanium oxide particles and the cuprous oxide particles combined; and 300 to 2000 parts by mass of an organic solvent per 100 parts by mass of the titanium oxide particles and the cuprous oxide particles combined. The titanium oxide particles and the cuprous oxide particles have an average primary particle diameter of 2 nm to 80 nm and have an average secondary particle diameter of 50 nm to 150 nm, the average secondary particle diameter being measured by dynamic light scattering using cumulant analysis. Moreover, 10 or more parts by mass of the titanium oxide particles are contained in 100 parts by mass of the non-volatile matter content of the copper complex titanium oxide dispersion liquid.

A coating agent composition according to a second aspect of the present invention includes: the copper complex titanium oxide dispersion liquid according to the first aspect; and a binder resin. 10 to 80 parts by mass of the titanium oxide particles are contained in 100 parts by mass of the non-volatile matter content of the coating agent composition.

A coating agent composition according to a third aspect of the present invention is the coating agent composition according to the second aspect in which the binder resin contains chlorinated polyolefin.

An antibacterial/antiviral member according to a fourth aspect of the present invention includes: a substrate; and a coating film which is provided on the substrate and includes the coating agent composition according to the second or third aspect.

An antibacterial/antiviral member according to a fifth aspect of the present invention is the antibacterial/antiviral member according to the fourth aspect in which the coating film has a static contact angle of 30 degrees or less for oleic acid.

DESCRIPTION OF EMBODIMENTS

Hereinafter, a copper complex titanium oxide dispersion liquid, a coating agent composition, and an antibacterial/antiviral member according to the embodiment of the present invention will be explained in detail below.

[Copper Complex Titanium Oxide Dispersion Liquid]

A copper complex titanium oxide dispersion liquid according to an embodiment of the present invention includes: titanium oxide particles; and 0.1 to 20 parts by mass of cuprous oxide particles per 100 parts by mass of the titanium oxide particles. The dispersion liquid further includes: 5 to 100 parts by mass of phosphate ester-based anionic surfactant per 100 parts by mass of the titanium oxide particles and the cuprous oxide particles combined; and 300 to 2000 parts by mass of organic solvent per 100 parts by mass of the titanium oxide particles and the cuprous oxide particles combined. The titanium oxide particles and the cuprous oxide particles have an average primary particle diameter of 2 nm to 80 nm and have an average secondary particle diameter of 50 nm to 150 nm as measured by dynamic light scattering using cumulant analysis. 10 or more parts by mass of the titanium oxide particles are contained in 100 parts by mass of the non-volatile matter content of the copper complex titanium oxide dispersion liquid.

The titanium oxide particles can be particles of anatase-type or rutile-type titanium oxide or can be a mixture of particles of anatase-type and rutile-type titanium oxide. Preferably, the titanium oxide particles are particles of anatase-type titanium oxide. Anatase-type titanium oxide has a larger band gap than rutile-type titanium oxide and is excellent in photocatalytic performance.

The particles of anatase-type titanium oxide may be mixed with amorphous titanium oxide. However, it is preferable that the amount of amorphous titanium oxide mixed is as small as possible because amorphous titanium oxide has poor photocatalytic activity. In order to enhance the photocatalytic activity, titanium oxide particles may be configured to support iron oxide or copper oxide on the surfaces thereof.

The average primary particle diameter of the titanium oxide particles is 2 nm to 80 nm. If the average primary particle diameter of the titanium oxide particles is less than 2 nm, the surface area of each titanium oxide particle is so small that the titanium oxide particles could be unlikely to exert the photocatalytic effect. If the average primary particle diameter of the titanium oxide particles is more than 80 nm, sufficiently ultrafine particles cannot be obtained by dispersion treatment described below. The titanium oxide particles could tend to aggregate and precipitate during the dispersion process or during storage after the dispersion process. The average primary particle diameter of titanium oxide particles can be calculated by measuring the diameter of plural titanium oxide particles with a transmission electronic microscope (TEM).

The average primary particle diameter of titanium oxide particles is preferably 5 nm to 50 nm and more preferably 5 nm to 30 nm. By having an average primary particle diameter in the aforementioned preferable range, the titanium oxide particles can be highly dispersed in an organic solvent while maintaining large surface area.

The copper complex titanium oxide dispersion liquid of the embodiment contains cuprous oxide particles in addition to the titanium oxide particles. Various types of copper compounds exhibiting an antibacterial activity have been reported. Copper (I) oxide (cuprous oxide, $Cu_2O$) has higher antibacterial and antiviral activities than copper (II) oxide (CuO). In other words, the cuprous oxide is more likely to release copper ions. The released copper ions come into contact with microorganisms to be combined with the enzyme or protein, reducing the activity of microorganisms. The metabolic function of microorganisms is therefore more likely to be inhibited. Moreover, the catalysis of the released copper ions activates oxygen in the air, facilitating decomposition of the organic matters of the microorganisms. Accordingly, the cuprous oxide particles are preferably composed of copper (I) oxide.

The average primary particle diameter of the cuprous oxide particles is 2 nm to 80 nm. If the average primary particle diameter of the cuprous oxide particles is less than 2 nm, the surface area of each cuprous oxide particle is so small that copper ions are less likely to be released. If the average primary particle diameter of the cuprous oxide particles is more than 80 nm, sufficiently ultrafine particles cannot be obtained by dispersion treatment described below. The cuprous oxide particles therefore could tend to aggregate and precipitate during the dispersion process or during storage after the dispersion process. The average primary particle diameter of cuprous oxide particles can be calculated by using a transmission electronic microscope (TEM) in a similar manner to titanium oxide particles.

The average primary particle diameter of cuprous oxide particles is preferably 10 nm to 70 nm and more preferably 30 nm to 60 nm. By having an average primary particle diameter in the aforementioned preferable or more preferable range, the cuprous oxide particles can be highly dispersed in an organic solvent while having large surface area.

The copper complex titanium oxide dispersion liquid of the embodiment contains the phosphate ester-based anionic surfactant in order to increase the dispersion of titanium oxide and cuprous oxide particles in the organic solvent. By using the phosphate ester-based anionic surfactant, the dispersion can be increased with the antibacterial and antiviral performances of the titanium oxide particles and the cuprous oxide particles prevented from being reduced. Examples of the phosphate ester-based anionic surfactant include alkyl phosphate salts, polyoxyethylene alkyl ether phosphate salts, and polyoxyethylene alkyl phenyl ether phosphate salts. More specific examples thereof include alkyl phosphate ester, polyoxyethylene alkyl ether phosphate ester, and polyoxyethylene (mono- or di-)alkyl phenyl ether phosphate ester. Other examples include phosphate ester of a polyoxyethylene (mono-, di- or tri-)alkyl phenyl ether polymer, and polyoxyethylene (mono-, di- or tri-)phenyl phenyl ether phosphate ester. Still other examples include polyoxyethylene (mono-, di- or tri-)benzyl phenyl ether phosphate ester, and polyoxyethylene (mono-, di- or tri-)styryl phenyl ether phosphate ester. Still other examples include phosphate ester of a polyoxyethylene (mono-, di- or tri-)styryl phenyl ether polymer, and phosphate ester of a polyoxyethylene polyoxypropylene block polymer. In addition, phosphate ester such as phosphatidylcholine, phosphatidyl ethanolimine, and condensed phosphoric acid (such as tripolyphosphate) may be used. Further, salts of the phosphate ester described above may also be used. Each of these materials used as the phosphate ester-based anionic surfactant may be used independently, or two or more kinds thereof may be combined together.

Although the organic solvent serving as a dispersion medium for the titanium oxide and cuprous oxide particles is not particularly limited, a solvent capable of easily volatilizing when being applied and suppressing hardening inhibition at the time of forming a coating film, is preferably selected as appropriate. Examples of the organic solvent include aromatic hydrocarbons (such as toluene and xylene), alcohols (such as methanol, ethanol, and isopropyl alcohol), and ketones (such as acetone, methyl ethyl ketone, and methyl isobutyl ketone). Other examples include aliphatic hydrocarbons (such as hexane and heptane), ethers (such as tetrahydrofuran), and amide solutions (such as N,N-dimethylformamide (DMF) and dimethylacetamide (DMAc)). Among these, the aromatic hydrocarbons and the alcohols are particularly preferable. Each of these materials used as the organic solvent may be used independently, or two or more kinds thereof may be combined together.

The added amount of cuprous oxide particles in the copper complex titanium oxide dispersion liquid can be properly controlled based on the content of titanium oxide particles. Specifically, the amount of cuprous oxide particles is 0.1 to 20 parts by mass per 100 parts by mass of titanium oxide particles. If the amount of cuprous oxide particles is less than 0.1 parts by mass, added cuprous oxide has no effect, and the antibacterial performance cannot be increased enough. If the amount of cuprous oxide particles is more than 20 parts by mass, the coating agent composition described later could have lower hardness.

More preferably, the added amount of cuprous oxide particles in the copper complex titanium oxide dispersion liquid is 0.1 to 10 parts by mass per 100 parts by mass of titanium oxide particles. When the amount of cuprous oxide particles is in the aforementioned more preferable range, the synergetic effect between the titanium oxide particles and the cuprous oxide particles can provide high antibacterial and antiviral performances. Moreover, the titanium oxide particles and the cuprous oxide particles can be more highly dispersed in the coating agent composition, and the coating agent composition has higher hardness.

The added amount of phosphate ester-based anionic surfactant in the copper complex titanium oxide dispersion liquid can be properly controlled based on the total content of titanium oxide and cuprous oxide particles. Specifically, the amount of phosphate ester-based anionic surfactant is set to 5 to 100 parts by mass per 100 parts by mass of the titanium oxide particles and the cuprous oxide particles combined. If the amount of phosphate ester-based anionic surfactant is less than 5 parts by mass, the titanium oxide particles and/or cuprous oxide particles tend to aggregate each other and cannot be dispersed sufficiently. When the amount of phosphate ester-based anionic surfactant is more than 100 parts by mass, curing inhibition could occur in the process of mixing the copper complex titanium oxide dispersion liquid with the binder resin to form a coating film as described later. When the amount of phosphate ester-based anionic surfactant is more than 100 parts by mass, moreover, the coating properties of the formed coating film, including film formation performance and adhesion, could be inadequate.

More preferably, the added amount of phosphate ester-based anionic surfactant is 5 to 90 parts by mass per 100 parts by mass of the titanium oxide particles and the cuprous oxide particles combined. When the amount of phosphate ester-based anionic surfactant is in the aforementioned more preferable range, the titanium oxide particles and the cuprous oxide particles are more highly dispersed while the coating properties of the coating film is prevented from being inadequate.

The added amount of organic solvent in the copper complex titanium oxide dispersion liquid can be also properly controlled based on the total content of titanium oxide and cuprous oxide particles. Specifically, the amount of organic solvent is set to 300 to 2000 parts by mass per 100 parts by mass of the titanium oxide particles and the cuprous oxide particles combined. When the amount of organic solvent is less than 300 parts by mass, the titanium oxide particles and the cuprous oxide particles are less dispersed. Moreover, higher viscosity of the copper complex titanium oxide dispersion liquid could reduce the efficiency of application work. When the amount of organic solvent is more than 2000 parts by mass, in the process of mixing the copper complex titanium oxide dispersion liquid with the binder resin to form the coating film, the inadequate film formation performance (drying properties) of the coating film could reduce the working efficiency.

More preferably, the added amount of organic solvent is 500 to 1800 parts by mass per 100 parts by mass of the titanium oxide particles and the cuprous oxide particles combined. When the amount of organic solvent is in the aforementioned more preferable range, the titanium oxide particles and the cuprous oxide particles are highly dispersed, and the viscosity of the copper complex titanium oxide dispersion liquid is prevented from becoming excessively high.

As described later, the copper complex titanium oxide dispersion liquid of the embodiment is mixed with the binder resin to form the coating agent composition. The coating agent composition is applied to a substrate to form an antibacterial and antiviral coating film. From the viewpoint of increasing the transparency of the coating film, the titanium oxide particles and the cuprous oxide particles in the copper complex titanium oxide dispersion liquid need to have an average secondary particle diameter of 50 nm to 150 nm. When the average secondary particle diameter is smaller than 50 nm, the primary particles having broken crystalline structures and the dispersed secondary particles exist together in the copper complex titanium oxide dispersion liquid because of excessive dispersion process. The photocatalytic activity and antibacterial performance could be therefore reduced. When the average secondary particle diameter is larger than 150 nm, the surface area of the titanium oxide particles and the cuprous oxide particles is so small that the photocatalytic activity and antibacterial performance could be lowered. Note that, in the present description, the average secondary particle diameter used is measured by a dynamic light scattering method and obtained by cumulant analysis.

In the copper complex titanium oxide dispersion liquid of the embodiment, 10 or more parts by mass of titanium oxide particles is contained in 100 parts by mass of the non-volatile matter content of the copper complex titanium oxide dispersion liquid. When the content of titanium oxide particles in 100 parts by mass of the total non-volatile matter content is lower than 10 parts by mass, an excessive amount of solvent component is included in the coating agent composition which is produced by mixing the copper complex titanium oxide dispersion liquid with the binder resin. The low content of titanium oxide particles in the coating agent composition can make it difficult to ensure high antibacterial performance. Moreover, the excessive amount of solvent component could cause dripping of the coating agent composition during application, resulting in abnormal appearance. Moreover, the coating film cannot be formed into sufficient thickness, and the coating properties thereof will be inadequate. The upper limit of the content of titanium oxide particles in the copper complex titanium oxide dispersion liquid is not particularly limited if the obtained coating film retains adequate transparency. The upper limit can be set to 50 parts by mass per 100 parts by mass of the non-volatile matter content of the copper complex titanium oxide dispersion liquid, for example.

The content of non-volatile matter content in this description is measured according to Japanese Industrial Standards JIS K5601-1-2 (Testing methods for paint components-Part 1: General rule-Section 2: Determination of non-volatile matter content). The elementary analysis for the non-volatile matter content calculates the contents of titanium oxide particles and cuprous oxide particles.

As described above, the copper complex titanium oxide dispersion liquid of the embodiment includes titanium oxide particles, cuprous oxide particles, a phosphate ester-based anionic surfactant, and an organic solvent. The content of cuprous oxide particles is 0.1 to 20 parts by mass per 100 parts by mass of titanium oxide particles. The content of phosphate ester-based anionic surfactant is 5 to 100 parts by mass and the content of organic solvent is 300 to 2000 parts by mass per 100 parts by mass of the titanium oxide particles and the cuprous oxide particles combined. In the copper complex titanium oxide dispersion liquid, the titanium oxide particles and the cuprous oxide particles have an average primary particle diameter of 2 nm to 80 nm and have an average secondary particle diameter of 50 nm to 150 nm as measured by dynamic light scattering using cumulant analysis. 10 or more parts by mass of the titanium oxide particles are contained in 100 parts by mass of the non-volatile matter content of the copper complex titanium oxide dispersion liquid. According to the aforementioned configuration, high dispersion of the titanium oxide particles and the cuprous oxide particles can be maintained even if the concentrations of the particles are increased. Accordingly, the antibacterial and antiviral coating film which is formed using such particles has transparency. Moreover, by including not only the titanium oxide particles but also the cuprous oxide particles, the copper complex titanium oxide dispersion liquid provides high antibacterial and antiviral performances.

[Manufacturing Method of Copper Complex Titanium Oxide Dispersion Liquid]

Next, a description is given of a method of manufacturing the copper complex titanium oxide dispersion liquid. The copper complex titanium oxide dispersion liquid can be prepared by mixing the aforementioned titanium oxide particles, cuprous oxide particles, phosphate ester-based anionic surfactant, and organic solvent and highly dispersing the titanium oxide particles and the cuprous oxide particles in the organic solvent. It is therefore possible to use any method capable of highly dispersing the titanium oxide particles and cuprous oxide particle. However, in order to increase dispersion of the titanium oxide particles and the cuprous oxide particles, the copper complex titanium oxide dispersion liquid is preferably produced by separately preparing a titanium oxide particle dispersion liquid and a cuprous oxide particle dispersion liquid and mixing the dispersion liquids.

<Titanium Oxide Particle Dispersion Liquid>

The titanium oxide particle dispersion liquid includes the aforementioned titanium oxide particles, phosphate ester-based anionic surfactant, and organic solvent. The titanium oxide particle dispersion liquid can be prepared by mixing the aforementioned titanium oxide particles, phosphate ester-based anionic surfactant, and organic solvent and highly dispersing the titanium oxide particles in the organic solvent. The titanium oxide particle dispersion liquid can be manufactured by any method capable of highly dispersing the titanium oxide particles.

From the viewpoint of increasing dispersion of the titanium oxide particles and easily implementing the transparency of the antibacterial and antiviral coating film, it is preferable that the process to disperse the titanium oxide particles is divided into a pre-dispersion treatment and a main dispersion treatment. This can wet the surfaces of the titanium oxide particles and replace the air layer on the surfaces with the organic solvent. Accordingly, the titanium oxide particles quickly disperse in the subsequent main dispersion treatment. When the pre-dispersion treatment is insufficient, dispersion proceeds slowly, and the titanium oxide particles could be subject to unnecessary mechanical shock. The broken crystalline structures of the titanium oxide particles could result in less stability of the dispersion liquid.

The pre-dispersion treatment can be performed by using a common dissolver for stirring. From the viewpoint of easily wetting the surfaces of the titanium oxide particles, it is preferable to use a high-speed stirrer for stirring. For example, T. K. Homomixer, T. K. Robomix, or T. K. Filmix (trade names, manufactured by PRIMIX Corporation) may be used as the high-speed stirrer. Alternatively, CLEAMIX (registered trademark) (trade name, manufactured by M Technique Co., Ltd.) or Ultradisper (trade name, manufactured by Asada Iron Works Co., Ltd.) may also be used.

A dispersing apparatus used in the main dispersion treatment may be a kneading machine such as a kneader, a two-roll mill, a three-roll mill, SS5 (trade name, manufactured by M Technique Co., Ltd.), and MIRACLE KCK (registered trademark) (trade name, manufactured by Asada Iron Works Co., Ltd.). Other examples of the dispersing apparatus include a ultrasonic dispersing machine, Microfluidizer (trade name, manufactured by Mizuho Industrial Co., Ltd.) as a high-pressure homogenizer, and NanoVater (registered trademark) (trade name, manufactured by Yoshida Kikai Co., Ltd.). Further, Starburst (registered trademark) (trade name, manufactured by Sugino Machine Ltd.) or G-smasher (trade name, Rix Corporation) may also be used. When bead media such as glass or zircon are used, a ball mill, a bead mill, a sand mill, a horizontal media mill dispersing apparatus, or a colloid mill may be used. Bead media used in a bead mill preferably have a diameter of 1 mm or smaller, more preferably have a diameter of 0.5 mm or smaller. Here, the dispersion time in the pre-dispersion treatment and the main dispersion treatment may be adjusted as appropriate depending on the type of the dispersing apparatus and media so that the titanium oxide particles are finely dispersed in the organic solvent together with the phosphate ester-based anionic surfactant.

In the process of supplying the processed liquid subjected to the pre-dispersion treatment to the aforementioned dispersing apparatus, the processed liquid may be simultaneously stirred sufficiently with a high-speed stirrer or the like. This can shorten the process time.

The added amount of the phosphate ester-based anionic surfactant in the titanium oxide particle dispersion liquid can be properly controlled based on the content of the titanium oxide particles. Specifically, the amount of phosphate ester-based anionic surfactant is preferably 1 to 30 parts by mass per 100 parts by mass of the titanium oxide particles. When the amount of phosphate ester-based anionic surfactant is less than 1 parts by mass, the titanium oxide particles tend to aggregate each other and cannot be dispersed sufficiently. When the amount of phosphate ester-based anionic surfactant is more than 30 parts by mass, curing inhibition could occur in the process of mixing the titanium oxide particle dispersion liquid with the cuprous oxide particle dispersion liquid and binder resin to form a coating film as described later. When the amount of phosphate ester-based anionic surfactant is more than 30 parts by mass, moreover, the coating properties of the formed coating film, including film formation performance and adhesion, could be inadequate.

More preferably, the added amount of phosphate ester-based anionic surfactant is 10 to 25 parts by mass per 100 parts by mass of the titanium oxide particles. When the amount of phosphate ester-based anionic surfactant is in the aforementioned more preferable range, the titanium oxide particles are highly dispersed, and the coating properties are prevented from becoming inadequate.

The added amount of organic solvent in the titanium oxide particle dispersion liquid can be properly controlled based on the content of titanium oxide particles. Specifically, the amount of organic solvent is preferably 500 to 2000 parts by mass per 100 parts by mass of titanium oxide particles. When the amount of organic solvent is less than 500 parts by mass, the titanium oxide particles could be less dispersed. When the amount of organic solvent is more than 2000 parts by mass, in the process of mixing the titanium oxide particle dispersion liquid with the cuprous oxide particle dispersion liquid and binder resin to form a coating film, inadequate film formation performance (drying performance) thereof could reduce the working efficiency.

More preferably, the added amount of organic solvent is 500 to 1000 parts by mass per 100 parts by mass of the titanium oxide particles. The amount of organic solvent is in the aforementioned more preferable range, the titanium oxide particles are highly dispersed, and the viscosity of the dispersion liquid is prevented from becoming excessively high.

As described later, the titanium oxide particle dispersion liquid of the embodiment is mixed with the cuprous oxide particle dispersion liquid and binder resin to form the coating agent composition. The coating agent composition is applied to a substrate to form an antibacterial and antiviral coating film. From the viewpoint of increasing the transparency of the coating film, the titanium oxide particles in the titanium oxide particle dispersion liquid need to have an average secondary particle diameter of 50 nm to 150 nm. When the average secondary particle diameter is smaller than 50 nm, the primary particles having broken crystalline structures and the dispersed secondary particles exist together in the titanium oxide particle dispersion liquid because of excessive dispersion process. This could reduce the photocatalytic activity. When the average secondary particle diameter is larger than 150 nm, the surface area of the titanium oxide particles is so small that the photocatalytic activity (antibacterial performance) thereof could be inadequate.

In the titanium oxide particle dispersion liquid of the embodiment, 10 or more parts by mass of the titanium oxide particles is contained in 100 parts by mass of the non-volatile matter content of the titanium oxide particle dispersion liquid preferably. When the content of titanium oxide particles in 100 parts by mass of the total non-volatile matter content is lower than 10 parts by mass, an excessive amount of solvent component is contained in the coating agent composition which is produced by mixing the titanium oxide particle dispersion liquid with the cuprous oxide particle dispersion liquid and binder resin. Accordingly, the low content of titanium oxide particles in the coating agent composition can make it difficult to ensure high antibacterial performance. Moreover, the excessive amount of solvent component could cause dripping of the coating agent composition during application, resulting in abnormal appearance. Moreover, the coating film cannot be formed into sufficient thickness, and the coating properties thereof could be inadequate. The content of titanium oxide particles in the titanium oxide particle dispersion liquid is not particularly limited if the obtained coating film retains adequate transparency. The content of titanium oxide particles in the titanium oxide particle dispersion liquid can be set to not higher than 50 parts by mass per 100 parts by mass of the non-volatile matter content of the titanium oxide particle dispersion liquid, for example.

<Cuprous Oxide Particle Dispersion Liquid>

The cuprous oxide particle dispersion liquid includes the aforementioned cuprous oxide particles, phosphate ester-based anionic surfactant, and organic solvent. The cuprous oxide particle dispersion liquid can be prepared by mixing the aforementioned cuprous oxide particles, phosphate ester-based anionic surfactant, and organic solvent and highly dispersing the cuprous oxide particles in the organic solvent. The preparation of the cuprous oxide particle dispersion liquid can employ any method capable of highly dispersing the cuprous oxide particles. From the viewpoint of increasing dispersion of the cuprous oxide particles and easily ensuring the transparency of the antibacterial and antiviral coating film, the process to disperse the cuprous oxide particles is preferably divided into a pre-dispersion treatment and a main dispersion treatment in a similar manner to the titanium oxide particle dispersion liquid. This can wet the surfaces of the cuprous oxide particles and replace the air layer thereon with the organic solvent. Accordingly, the cuprous oxide particles quickly disperse in the subsequent main dispersion treatment.

The added amount of the phosphate ester-based anionic surfactant in the cuprous oxide particle dispersion liquid can be properly controlled based the content of the cuprous oxide particles. Specifically, the amount of phosphate ester-based anionic surfactant is preferably 10 to 100 parts by mass per 100 parts by mass of the cuprous oxide particles. When the amount of phosphate ester-based anionic surfactant is less than 10 parts by mass, the cuprous oxide particles tend to aggregate each other and could not be dispersed sufficiently. When the amount of phosphate ester-based anionic surfactant is more than 100 parts by mass, curing inhibition could occur in the process of mixing the cuprous oxide particle dispersion liquid with the titanium oxide particle dispersion liquid and binder resin to form a coating film. When the amount of phosphate ester-based anionic surfactant is more than 100 parts by mass, moreover, the coating properties of the formed coating film, including film formation performance and adhesion, could be inadequate.

The added amount of phosphate ester-based anionic surfactant in the cuprous oxide particle dispersion liquid is more preferably 20 to 90 parts by mass per 100 parts by mass of the cuprous oxide particles and especially preferably 30 to 70 parts by mass. When the amount of phosphate ester-based anionic surfactant is in the above more preferable or especially preferable range, the cuprous oxide particles are highly dispersed, and the coating properties are prevented from becoming inadequate.

The added amount of organic solvent in the cuprous oxide particle dispersion liquid can be properly controlled based on the content of cuprous oxide particles. Specifically, the amount of organic solvent is preferably 500 to 10000 parts by mass per 100 parts by mass of cuprous oxide particles. When the amount of organic solvent is less than 500 parts by mass, the cuprous oxide particles could be less dispersed. Moreover, high viscosity of the cuprous oxide particle dispersion liquid could reduce the efficiency of application work. When the amount of organic solvent is more than 10000 parts by mass, in the process of mixing the cuprous oxide particle dispersion liquid with the titanium oxide particle dispersion liquid and binder resin to form a coating film, inadequate film formation performance (drying properties) thereof could reduce the working efficiency.

More preferably, the added amount of organic solvent is 1000 to 5000 parts by mass per 100 parts by mass of the titanium oxide particles. When the amount of organic solvent is in the more preferable range above, the cuprous oxide particles are highly dispersed, and the viscosity of the dispersion liquid is prevented from becoming excessively high.

As described later, the cuprous oxide particle dispersion liquid of the embodiment is mixed with the titanium oxide particle dispersion liquid and binder resin to form the coating agent composition. The coating agent composition is applied to a substrate to form an antibacterial and antiviral coating film. From the viewpoint of increasing transparency of the coating film, the cuprous oxide particles in the cuprous oxide particle dispersion liquid need to have an average secondary particle diameter of 50 nm to 150 nm. When the average secondary particle diameter is smaller than 50 nm, the primary particles having broken crystalline structures and the dispersed secondary particles exist together in the cuprous oxide particle dispersion liquid because of excessive dispersion process. This could reduce the antibacterial performance. When the average secondary particle diameter is larger than 150 nm, the surface area of the cuprous oxide particles could be so small that the antibacterial performance thereof be inadequate.

<Copper Complex Titanium Oxide Dispersion Liquid>

The copper complex titanium oxide dispersion liquid of the embodiment is produced by mixing the titanium oxide particle dispersion liquid and cuprous oxide particle dispersion liquid prepared as described above in the above-described amounts. The process of mixing the titanium oxide particle dispersion liquid and the cuprous oxide particle dispersion liquid can use the above-described high-speed stirrer.

[Coating Agent Composition]

The coating agent composition according to the embodiment includes the aforementioned copper complex titanium oxide dispersion liquid and binder resin. As described above, the copper complex titanium oxide dispersion liquid of the embodiment includes both titanium oxide and cuprous oxide which are highly dispersed. The coating agent composition including the thus-configured copper complex titanium oxide dispersion liquid can form a coating film with high antibacterial and antiviral performances and high transparency.

The binder resin mixed together with the copper complex titanium oxide dispersion liquid is not particularly limited if the binder resin ensures the stability, antibacterial and antiviral performances, and transparency of the coating film obtained from the coating agent composition. Examples of the binder resin include alkyd resin, acrylic resin, melamine resin, urethane resin, epoxy resin, and silicone resin. In addition, polyester resin, polyamic acid resin, polyimide resin, styrene-maleic acid resin, or styrene-maleic anhydride resin may also be used. Further, various types of acrylic monomers or acrylate monomers may be applicable. Particularly preferable examples of resin or a monomer as the binder resin include urethane resin, acrylic resin, acrylic monomers, polyamic acid resin, polyimide resin, styrene-maleic acid resin, and styrene-maleic anhydride resin. Each of these materials used as the binder resin may be used independently, or two or more kinds thereof may be combined together.

The above described binder resin preferably includes at least one of an alkyl group with 5 to 23 carbon atoms and an aromatic ring as a functional group. The binder resin including such a functional group can give lipophilic properties to the coating surface of the antibacterial/antiviral member. Accordingly, the lipid component of fingerprints adhering to the coating film, for example, can easily diffuse in the interface of the lipophilic coating surface. This can make smudge due to adhering lipid components invisible or less visible.

As described above, when the binder resin includes an alkyl group, the number of carbon atoms in the alkyl group is preferably 5 to 23. Even if the number of carbon atoms in the alkyl group is out of this range, the alkyl group can give lipophilic properties and exert the aforementioned effects. However, when the number of carbon atoms in the alkyl group is less than 5, the lipophilic properties of the antibacterial/antiviral member could be a little inadequate. When the number of carbon atoms is more than 23, the binder resin is difficult to handle. This could prevent the coating agent composition from exerting stable performance. When the binder resin includes an aromatic ring as the functional group, the aromatic ring is not particularly limited and can be a phenyl group, an amino phenyl group, or the like.

In addition to the aforementioned resin, the binder resin may include a chlorinated polyolefin. The substrate to which the coating agent composition is applied is not particularly limited as described later. When the substrate is made of polyolefin, the coating film made of the coating agent composition has lower adhesion to the substrate because polyolefin, such as polyethylene and polypropylene, has low surface free energy. However, addition of chlorinated polyolefin in the binder resin can increase the adhesion of the coating film to the polyolefin substrate.

The content of chlorinated polyolefin is preferably 20 to 50 parts by mass per 100 parts by mass of binder component and more preferably 30 to 40 parts by mass. Setting the content of chlorinated polyolefin in the aforementioned preferable or more preferable range can increase the long-term storage stability of the coating agent composition and increase the mechanical strength and adhesive force of the coating film made of the coating agent composition.

Herein, the content of chlorine in 100 parts by mass of chlorinated polyolefin is preferably 20 to 30 parts by mass and more preferably 25 to 30 parts by mass. When the binder resin is composed of acrylic resin and chlorinated polyolefin, setting the content of chlorine in the aforementioned range can prevent the coating agent composition from increasing in viscosity or generating gel matters during storage, and can stabilize the coating agent composition. Moreover, the coating film made of the thus-configured coating agent composition tends to have higher adhesion performance to polyolefin such as polyethylene and polypropylene.

Examples of chlorinated polyolefins which can be contained in the binder resin include chlorinated polyethylene, chlorinated polypropylene, chlorinated polybutadiene, chlorinated ethylene-propylene copolymer, and chlorinated ethylene-vinyl acetate copolymer. The binder resin may include one of these chlorinated polyolefins alone or a combination of two or more thereof.

Moreover, in addition to the copper complex titanium oxide dispersion liquid and binder resin, the coating agent composition may include various types of additives without departing from the range that cannot affect the antibacterial activity. Specifically, the coating agent composition may include a dispersant, a pigment, a filler, an aggregate, a thickener, a flow control agent, a leveling agent, a curing agent, a cross-linker, a curing catalyst, and the like.

The coating agent composition according to the embodiment can be prepared by mixing the aforementioned copper complex titanium oxide dispersion liquid and binder resin and further mixing the aforementioned additives when needed. In the mixing process, the above-described dissolver or high-speed stirrer can be used for mixing, for example.

In the coating agent composition, preferably 10 to 80 parts by mass of titanium oxide particles are contained in 100 parts by mass of the non-volatile matter content of the coating agent composition. When the content of titanium oxide particles is lower than 10 parts by mass in the non-volatile matter content of the coating agent composition, the coating film could have an inadequate antibacterial performance and have low hardness. When the content of titanium oxide particles is more than 80 parts by mass, the coating film has adequate antibacterial performance, but shortage of the binder resin could reduce the coating properties thereof. The coating film also could have poor transparency.

In the coating agent composition, more preferably 30 to 70 parts by mass per titanium oxide particles or especially preferably 40 to 60 parts by mass are contained 100 parts by mass of the non-volatile matter content of the coating agent composition. By setting the content of titanium oxide particles in the aforementioned more preferable or especially more preferable range, the coating film has sufficient antibacterial and antiviral performances. Moreover, the coating properties of the coating film are prevented from becoming inadequate, and the coating film retains high transparency.

In the coating agent composition, preferably 0.1 to 10 parts by mass or especially preferably 0.1 to 5 parts by mass of cuprous oxide particles are contained in 100 parts by mass of the non-volatile matter content of the coating agent composition. By setting the content of cuprous oxide particles in the aforementioned more preferable or especially preferable range, the coating film has sufficient antibacterial and antiviral performances by the synergetic effect between cuprous and titanium oxide particles. Moreover, the coating properties of the coating film are prevented from becoming inadequate, and the coating film retains high transparency.

[Antibacterial/Antiviral Member]

The antibacterial/antiviral member according to the embodiment includes a substrate and a coating film which is provided on the substrate and includes the coating agent composition. As described above, the coating agent composition of the embodiment has high antibacterial and antiviral performances due to the titanium oxide particles and the cuprous oxide particles and also has antifouling and deodorization effects. Moreover, the titanium oxide particles and the cuprous oxide particles are highly dispersed in the coating agent composition, so that the obtained coating film has high transparency.

In the present embodiment, the substrate may basically include any material such as an organic polymer, ceramics, metal, glass, plastic, decorative plywood, or composites of these materials. The shape of the substrate is not particularly limited and may be a simple or complicated shape such as a plate shape, a spherical shape, a round column, a cylindrical shape, a rod shape, a prism, or a hollow prism. Alternatively, the substrate may be a porous body such as a filter.

The substrate is preferably used for construction materials such as ceiling materials, tiles, glass, wallpaper, wall materials, floors, or fixture materials, interior materials for vehicles (instrument panels, seats, or ceilings), electrical appliances such as refrigerators or air conditioners, textile products such as clothing or curtains, industrial equipment, or medical equipment. The substrate is also preferably used for doors, door handles, pulls, railings, interior counters, furniture, kitchens, toilets, bath rooms, lighting fixtures, touch panels, switches, or sheets used therein. The coating film including the coating agent composition according to the present embodiment is particularly effectively used for surfaces on which human bodies or the like frequently touch due to the high antibacterial/antiviral property of the coating film.

The antibacterial/antiviral material according to the present embodiment may be applied to filters for air purifiers or for air conditioners. The antibacterial/antiviral material is effective when used not only in houses but also in other places where large numbers of people use such as hospitals and homes for elderly people, and public transportation such as trains, buses, and planes, since the use of the antibacterial/antiviral material can reduce the risk of a bacterial or viral infection.

The antibacterial/antiviral member according to the present embodiment can be obtained in a manner such that the coating agent composition is applied to the substrate and is then dried. The applying method and the drying method in this case are not particularly limited. Examples of the method of applying the coating agent composition to at least part of the substrate include screen printing, spin coating, dip coating, roll coating, brush coating, spray coating, and ink jet coating. The drying conditions are not particularly limited as long as the organic solvent can be removed.

After drying, the coating agent composition may be exposed to ultraviolet irradiation. The obtained coating film can be thereby cured, and the hardness thereof can be increased.

The thickness of the coating film made of the applied coating agent composition is preferably 2 µm to 15 µm and more preferably 4 µm to 13 µm after curing. When the cured coating film has a thickness in this range, the coating film has high surface hardness and high adhesion.

As described above, the antibacterial/antiviral member of the embodiment includes a substrate and a coating film which is provided on the substrate and includes the coating agent composition. In the coating agent composition, nanoparticles of titanium oxide and cuprous oxide are dispersed with high concentrations. Accordingly, the antibacterial/antiviral member can have high antibacterial and antiviral performances due to the titanium oxide particles and the cuprous oxide particles and also have transparency.

Moreover, the binder resin contained in the coating film of the antibacterial/antiviral member may include at least one of an alkyl group with 5 to 23 carbon atoms and an aromatic ring as the functional group. The binder resin, which has such a lipophilic group, can make smudge due to lipid components of fingerprints invisible and less visible, so that the antibacterial/antiviral member has an excellent fingerprint resistance. In this case, the static contact angle of the coating film with respect to oleic acid is preferably 30 degrees or less and more preferably 15 degrees or less. The lower limit of the static contact angle thereof for oleic acid is not particularly limited but is preferably 1 degree or more.

The binder resin contained in the coating film of the antibacterial/antiviral member may contain chlorinated polyolefin. When the binder resin contains chlorinated polyolefin, it is unnecessary to perform pretreatment, such as application of a primer, for the substrate made of less-adhesive polyolefin or the like and the coating agent composition can be applied directly to the substrate.

EXAMPLES

Hereinafter, a description is given of examples and comparative examples of the present invention in more detail, but the present invention is not limited to the examples.

Example 1

Preparation of Titanium Oxide Particle Dispersion Liquid

First, as the titanium oxide particles, ST-01 by ISHIHARA SANGYO KAISHA, LTD. (average primary particle diameter: 7 nm, crystalline structure: anatase) is prepared. As an organic solvent, methyl ethyl ketone (MEK) is prepared. As the phosphate ester-based anionic surfactant, DISPARLON (registered trademark) PW-36 by Kusumoto Chemicals, Ltd. is prepared.

Next, 100 parts by mass of the titanium oxide particles, 800 parts by mass of methyl ethyl ketone, and 10 parts by mass of the phosphate ester-based anionic surfactant are mixed and then stirred at 8000 rpm for 30 minutes using a stirrer as the pre-dispersion treatment. The stirrer is T. K. Robomix by PRIMIX Corporation.

Thereafter, 1 L of the processed liquid obtained by the pre-dispersion treatment is stirred at 3000 rpm using the stirrer (T. K. Robomix by PRIMIX Corporation), followed by the main dispersion treatment using a disperser (PICO-MILL by Asada Iron Works Co., Ltd.). The dispersion process is performed for two-hour circulation using 0.3 mm-zirconia beads as the dispersion media of the disperser. The thus-prepared titanium oxide particle dispersion liquid has a titanium oxide concentration of 11% by mass.

<Preparation of Cuprous Oxide Particle Dispersion Liquid>

First, as the cuprous oxide particles, cuprous oxide (average primary particle diameter: 50 nm, CuO reduction) by Sigma-Aldrich Corporation is prepared. As the organic solvent, methyl ethyl ketone (MEK) is prepared. As the phosphate ester-based anionic surfactant, DISPARLON (registered trademark) PW-36 (by Kusumoto Chemicals, Ltd.) is prepared.

Next, 100 parts by mass of the cuprous oxide particles, 2500 parts by mass of methyl ethyl ketone, and 50 parts by mass of the phosphate ester-based anionic surfactant are mixed and then stirred at 8000 rpm for 30 minutes using a stirrer as the pre-dispersion treatment. The stirrer is T. K. Robomix by PRIMIX Corporation.

Thereafter, 1 L of the processed liquid obtained by the pre-dispersion treatment is stirred at 3000 rpm using the stirrer (T. K. Robomix by PRIMIX Corporation), followed by the main dispersion treatment using a disperser (PICO-MILL by Asada Iron Works Co., Ltd.). The dispersion process is performed for two-hour circulation using 0.3 mm-zirconia beads as the dispersion media of the disperser. The thus-prepared cuprous oxide particle dispersion liquid has a titanium oxide concentration of 4% by mass.

<Preparation of Coating Agent Composition>

455 parts by mass of the prepared titanium oxide particle dispersion liquid and 27 parts by mass of the prepared cuprous oxide particle dispersion liquid, and 245 parts by mass of the binder resin are mixed and then stirred using a stirrer to prepare a coating agent composition of Example 1. The binder resin is resin shown below.

First, ACRYDIC (registered trademark) A801 by DIC Corporation as isocyanate curing acrylic resin is mixed with DURANATE (registered trademark) TPA100 by Asahi Kasei Chemicals Corporation in a manner such that an isocyanate group and a hydroxyl group fulfilled the condition of NCO/OH=1. Next, the obtained mixture is diluted with methyl ethyl ketone so that the non-volatile matter content thereof is 20% by mass, thus preparing the binder resin.

Example 2

The titanium oxide particle dispersion liquid is prepared in the same manner as Example 1 except that 100 parts by mass of the titanium oxide particles, 1800 parts by mass of methyl ethyl ketone, and 10 parts by mass of the phosphate ester-based anionic surfactant are mixed. The concentration of titanium oxide in the titanium oxide particle dispersion liquid is 5% by mass.

Subsequently, 955 parts by mass of the prepared titanium oxide particle dispersion liquid, 27 parts by mass of the cuprous oxide particle dispersion liquid prepared in Example 1, and 245 parts by mass of the binder resin are mixed in the same manner as Example 1, thus preparing the coating agent composition of Example 2.

Example 3

The titanium oxide particle dispersion liquid is prepared in the same manner as Example 1 except that 100 parts by mass of the titanium oxide particles, 300 parts by mass of methyl ethyl ketone, and 10 parts by mass of the phosphate ester-based anionic surfactant are mixed. The concentration of titanium oxide in the titanium oxide particle dispersion liquid is 24% by mass.

Subsequently, 205 parts by mass of the above titanium oxide particle dispersion liquid, 27 parts by mass of the cuprous oxide particle dispersion liquid prepared in Example 1, and 245 parts by mass of the binder resin are mixed in the same manner as Example 1, thus preparing the coating agent composition of Example 3.

Example 4

The cuprous oxide particle dispersion liquid is prepared in the same manner as Example 1 except that 100 parts by mass of the cuprous oxide particles, 10000 parts by mass of methyl ethyl ketone, and 50 parts by mass of the phosphate ester-based anionic surfactant are mixed. The concentration of cuprous oxide in the cuprous oxide particle dispersion liquid is 1% by mass.

Subsequently, 455 parts by mass of the titanium oxide particle dispersion liquid prepared in Example 1, 102 parts by mass of the above cuprous oxide particle dispersion liquid, and 245 parts by mass of the binder resin are mixed in the same manner as Example 1, thus preparing the coating agent composition of Example 4.

Example 5

The cuprous oxide particle dispersion liquid is prepared in the same manner as Example 1 except that 100 parts by mass of the cuprous oxide particles, 800 parts by mass of methyl ethyl ketone, and 50 parts by mass of the phosphate ester-based anionic surfactant are mixed. The concentration of cuprous oxide in the cuprous oxide particle dispersion liquid is 11% by mass.

Subsequently, 455 parts by mass of the titanium oxide particle dispersion liquid prepared in Example 1, 10 parts by mass of the above cuprous oxide particle dispersion liquid, and 245 parts by mass of the binder resin are mixed in the same manner as Example 1, thus preparing the coating agent composition of Example 5.

Example 6

The titanium oxide particle dispersion liquid is prepared in the same manner as Example 1 except that 100 parts by mass of the titanium oxide particles, 800 parts by mass of methyl ethyl ketone, and 25 parts by mass of the phosphate ester-based anionic surfactant are mixed. The concentration of titanium oxide in the titanium oxide particle dispersion liquid is 11% by mass.

Subsequently, 453 parts by mass of the above titanium oxide particle dispersion liquid, 27 parts by mass of the cuprous oxide particle dispersion liquid prepared in Example 1, and 245 parts by mass of the binder resin are mixed in the same manner as Example 1, thus preparing the coating agent composition of Example 6.

Example 7

The titanium oxide particle dispersion liquid is prepared in the same manner as Example 1 except that 100 parts by mass of the titanium oxide particles, 800 parts by mass of methyl ethyl ketone, and 5 parts by mass of the phosphate ester-based anionic surfactant are mixed. The concentration of titanium oxide in the titanium oxide particle dispersion liquid is 11% by mass.

Subsequently, 453 parts by mass of the above titanium oxide particle dispersion liquid, 27 parts by mass of the cuprous oxide particle dispersion liquid prepared in Example 1, and 245 parts by mass of the binder resin are mixed in the same manner as Example 1, thus preparing the coating agent composition of Example 7.

Example 8

The cuprous oxide particle dispersion liquid is prepared in the same manner as Example 1 except that 100 parts by mass of the cuprous oxide particles, 2500 parts by mass of methyl ethyl ketone, and 70 parts by mass of the phosphate ester-based anionic surfactant are mixed. The concentration of cuprous oxide in the cuprous oxide particle dispersion liquid is 4% by mass.

Subsequently, 455 parts by mass of the titanium oxide particle dispersion liquid prepared in Example 1, 27 parts by mass of the above cuprous oxide particle dispersion liquid, and 245 parts by mass of the binder resin are mixed in the same manner as Example 1, thus preparing the coating agent composition of Example 8.

Example 9

The cuprous oxide particle dispersion liquid is prepared in the same manner as Example 1 except that 100 parts by mass of the cuprous oxide particles, 2500 parts by mass of methyl ethyl ketone, and 20 parts by mass of the phosphate ester-based anionic surfactant are mixed. The concentration of cuprous oxide in the cuprous oxide particle dispersion liquid is 4% by mass.

Subsequently, 455 parts by mass of the titanium oxide particle dispersion liquid prepared in Example 1, 26 parts by mass of the above cuprous oxide particle dispersion liquid, and 245 parts by mass of the binder resin are mixed in the same manner as Example 1, thus preparing the coating agent composition of Example 9.

Example 10

The coating agent composition of Example 10 is prepared in the same manner as Example 1 except that 182 parts by mass of the titanium oxide particle dispersion liquid, 27 parts by mass of the cuprous oxide particle dispersion liquid, and 245 parts by mass of the binder resin are mixed.

Example 11

The coating agent composition of Example 11 is prepared in the same manner as Example 1 except that 819 parts by mass of the titanium oxide particle dispersion liquid, 27 parts by mass of the cuprous oxide particle dispersion liquid, and 45 parts by mass of the binder resin are mixed.

Example 12

The coating agent composition of Example 12 is prepared in the same manner as Example 1 except that 455 parts by mass of the titanium oxide particle dispersion liquid, 13 parts by mass of the cuprous oxide particle dispersion liquid, and 248 parts by mass of the binder resin are mixed.

Example 13

The coating agent composition of Example 13 is prepared in the same manner as Example 1 except that 455 parts by mass of the titanium oxide particle dispersion liquid, 212 parts by mass of the cuprous oxide particle dispersion liquid, and 210 parts by mass of the binder resin are mixed.

Example 14

455 parts by mass of the titanium oxide particle dispersion liquid prepared in Example 1 and 27 parts by mass of the cuprous oxide particle dispersion liquid prepared in Example 1 are mixed with 245 parts by mass of the binder resin. Next, the obtained mixture is diluted with methyl ethyl ketone so that the non-volatile matter content is 20% by mass. The diluted mixture is stirred by a stirrer, thus preparing the coating agent composition of Example 14. The binder resin is a mixture of 100 parts by mass of UV curable resin BEAMSET 1461 by Arakawa Chemical Industries, Ltd. and 15 parts by mass of photopolymerization initiator IRGACURE 184 by BASF.

Example 15

First, 15 parts by mass of HARDLEN (registered trademark) 13-LP by TOYOBO CO., LTD. (chlorine content: 26% by mass, solid content: 100%) as chlorinated polyolefin and 85 parts by mass of methyl ethyl ketone as the solvent are mixed to prepare chlorinated polyolefin solution.

Next, 455 parts by mass of the titanium oxide particle dispersion liquid prepared in Example 1, 27 parts by mass of the cuprous oxide particle dispersion liquid prepared in Example 1, 122.5 parts by mass of the binder resin, and 122.5 parts by mass of the chlorinated polyolefin solution are mixed and stirred by a stirrer. The coating agent composition of Example 15 is thus prepared.

Comparative Example 1

The titanium oxide particle dispersion liquid is prepared in the same manner as Example 1 except that 100 parts by mass of the titanium oxide particles, 2500 parts by mass of methyl ethyl ketone, and 10 parts by mass of the phosphate ester-based anionic surfactant are mixed. The concentration of titanium oxide in the titanium oxide particle dispersion liquid is 4% by mass.

Subsequently, 1305 parts by mass of the titanium oxide particle dispersion liquid prepared above, 27 parts by mass of the cuprous oxide particle dispersion liquid prepared in Example 1, and 245 parts by mass of the binder resin are mixed in the same manner as Example 1, preparing the coating agent composition of Comparative Example 1.

Comparative Example 2

First, the titanium oxide particles, methyl ethyl ketone, phosphate ester-based anionic surfactant are prepared in the same manner as Example 1. Next, 100 parts by mass of the titanium oxide particles, 800 parts by mass of the methyl ethyl ketone, and 100 parts by mass of the phosphate ester-based anionic surfactant are mixed and then stirred at 8000 rpm for 30 minutes using a stirrer as the pre-dispersion treatment. The stirrer is T. K. Robomix by PRIMIX Corporation.

Thereafter, 1 L of the processed liquid obtained by the pre-dispersion treatment is stirred at 3000 rpm using the stirrer (T. K. Robomix by PRIMIX Corporation). Subsequently, the main dispersion treatment is tried using a disperser (PICOMILL by Asada Iron Works Co., Ltd.). However, the viscosity of the processed liquid obtained in the pre-dispersion treatment is not lowered enough to allow the processed liquid to be supplied to the disperser, and the main dispersion treatment cannot be carried out. Accordingly, the titanium oxide particle dispersion liquid cannot be prepared, and the coating agent composition of Comparative Example 2 cannot be prepared.

Comparative Example 3

The cuprous oxide particle dispersion liquid is prepared in the same manner as Example 1 except that 100 parts by mass of the cuprous oxide particles, 15000 parts by mass of methyl ethyl ketone, and 50 parts by mass of the phosphate ester-based anionic surfactant are mixed. The concentration of cuprous oxide in the cuprous oxide particle dispersion liquid is 1% by mass.

Subsequently, 455 parts by mass of the titanium oxide particle dispersion liquid prepared in Example 1, 152 parts by mass of the cuprous oxide particle dispersion liquid prepared above, and 245 parts by mass of the binder resin are mixed in the same manner as Example 1, preparing the coating agent composition of Comparative Example 3.

Comparative Example 4

First, the cuprous oxide particles, methyl ethyl ketone, phosphate ester-based anionic surfactant are prepared in the same manner as Example 1. Next, 100 parts by mass of the cuprous oxide particles, 100 parts by mass of the methyl ethyl ketone, and 50 parts by mass of the phosphate ester-based anionic surfactant are mixed and then stirred at 8000 rpm for 30 minutes using a stirrer (T. K. Robomix by PRIMIX Corporation) as the pre-dispersion treatment.

Thereafter, 1 L of the processed liquid obtained by the pre-dispersion treatment is stirred at 3000 rpm using the stirrer (T. K. Robomix by PRIMIX Corporation). Subsequently, the main dispersion treatment is tried with a disperser (PICOMILL by Asada Iron Works Co., Ltd.). However, the viscosity of the processed liquid obtained in the pre-dispersion treatment is not lowered enough to allow the processed liquid to be supplied to the disperser, and the main dispersion treatment cannot be carried out. Accordingly, the cuprous oxide particle dispersion liquid cannot be prepared, and the coating agent composition of Comparative Example 4 cannot be prepared.

Comparative Example 5

The titanium oxide particle dispersion liquid is prepared in the same manner as Example 1 except that 100 parts by mass of the titanium oxide particles, 800 parts by mass of methyl ethyl ketone, and 50 parts by mass of the phosphate ester-based anionic surfactant are mixed. The concentration of titanium oxide in the titanium oxide particle dispersion liquid is 11% by mass.

Subsequently, 475 parts by mass of the titanium oxide particle dispersion liquid prepared above, 27 parts by mass of the cuprous oxide particle dispersion liquid prepared in Example 1, and 245 parts by mass of the binder resin are mixed in the same manner as Example 1, preparing the coating agent composition of Comparative Example 5.

Comparative Example 6

First, the titanium oxide particles, methyl ethyl ketone, phosphate ester-based anionic surfactant are prepared in the same manner as Example 1. Next, 100 parts by mass of the titanium oxide particles, 800 parts by mass of the methyl ethyl ketone, and 0.5 parts by mass of the phosphate ester-based anionic surfactant are mixed and then stirred at 8000 rpm for 30 minutes using a stirrer as the pre-dispersion treatment. The stirrer is T. K. Robomix by PRIMIX Corporation.

Thereafter, 1 L of the processed liquid obtained by the pre-dispersion treatment is stirred at 3000 rpm using a stirrer (T. K. Robomix by PRIMIX Corporation). Subsequently, the main dispersion treatment is tried with a disperser (PICOMILL by Asada Iron Works Co., Ltd.). However, the viscosity of the processed liquid obtained in the pre-dispersion treatment is not lowered enough to allow the processed liquid to be supplied to the disperser, and the main dispersion treatment cannot be carried out. Accordingly, the titanium oxide particle dispersion liquid cannot be prepared, and the coating agent composition of Comparative Example 6 cannot be prepared.

Comparative Example 7

The cuprous oxide particle dispersion liquid is prepared in the same manner as Example 1 except that 100 parts by mass of the cuprous oxide particles, 2500 parts by mass of methyl ethyl ketone, and 200 parts by mass of the phosphate ester-based anionic surfactant are mixed. The concentration of cuprous oxide in the cuprous oxide particle dispersion liquid is 4% by mass.

Subsequently, 455 parts by mass of the titanium oxide particle dispersion liquid prepared in Example 1, 28 parts by mass of the cuprous oxide particle dispersion liquid prepared above, and 245 parts by mass of the binder resin are mixed in the same manner as Example 1, preparing the coating agent composition of Comparative Example 7.

Comparative Example 8

First, the cuprous oxide particles, methyl ethyl ketone, phosphate ester-based anionic surfactant are prepared in the same manner as Example 1. Next, 100 parts by mass of the cuprous oxide particles, 2500 parts by mass of the methyl ethyl ketone, and 5 parts by mass of the phosphate ester-based anionic surfactant are mixed and then stirred at 8000 rpm for 30 minutes using a stirrer (T. K. Robomix by PRIMIX Corporation) as the pre-dispersion treatment.

Thereafter, 1 L of the processed liquid obtained by the pre-dispersion treatment is stirred at 3000 rpm using the stirrer (T. K. Robomix by PRIMIX Corporation). Subsequently, the main dispersion treatment is tried with a disperser (PICOMILL by Asada Iron Works Co., Ltd.). However, the viscosity of the processed liquid obtained in the pre-dispersion treatment is not lowered enough to allow the processed liquid to be supplied to the disperser, and the main dispersion treatment cannot be carried out. Accordingly, the cuprous oxide particle dispersion liquid cannot be prepared, and the coating agent composition of Comparative Example 8 cannot be prepared.

Comparative Example 9

27 parts by mass of the cuprous oxide particle dispersion liquid prepared in Example 1 and 495 parts by mass of the binder resin are mixed and then stirred by a stirrer, thus preparing the coating agent composition of Comparative Example 9. In other words, the titanium oxide particle dispersion liquid is not used in Comparative Example 9.

Comparative Example 10

The coating agent composition of Comparative Example 10 is prepared in the same manner as Example 1 except that 865 parts by mass of the titanium oxide particle dispersion liquid, 27 parts by mass of the cuprous oxide particle dispersion liquid, and 20 parts by mass of the binder resin are mixed.

Comparative Example 11

455 parts by mass of the titanium oxide particle dispersion liquid prepared in Example 1 and 250 parts by mass of the binder resin are mixed and stirred by a stirrer, thus preparing the coating agent composition of Comparative Example 11. In other words, the cuprous oxide particle dispersion liquid is not used in Comparative Example 11.

Comparative Example 12

The coating agent composition of Comparative Example 12 is prepared in the same manner as Example 1 except that 455 parts by mass of the titanium oxide particle dispersion liquid, 530 parts by mass of the cuprous oxide particle dispersion liquid, and 250 parts by mass of the binder are mixed.

Comparative Example 13

The coating agent composition of Comparative Example 13 is prepared in the same manner as Example 1 except that the surfactant is DISPERBYK (registered trademark)-111 (ionic surfactant) by BYK-Chemie Japan K. K.

Tables 1 and 2 show the added amounts of titanium oxide particles, organic solvent, and surfactant in the titanium oxide particle dispersion liquid of the examples and comparative examples and the concentrations of titanium oxide particles in the titanium oxide particle dispersion liquid. Tables 1 and 2 also show the amounts of cuprous oxide particles, organic solvent, and surfactant in the cuprous oxide particle dispersion liquid in the examples and comparative examples and the concentrations of cuprous oxide particles in the cuprous oxide particle dispersion liquid. Moreover, Tables 1 and 2 show the amounts of the titanium oxide particle dispersion liquid, cuprous oxide particle dispersion liquid, and binder resin mixed in the coating agent composition.

TABLE 1

| | Titanium Oxide Particle Dispersion Liquid | | | | Cuprous Oxide Particle Dispersion Liquid | | | | Mixed Amount of Titanium Oxide Particle Dispersion Liquid (Parts by Mass) | Mixed Amount of Cuprous Oxide Particle Dispersion Liquid (Parts by Mass) | Mixed Amount of Binder Resin (Parts by Mass) |
|---|---|---|---|---|---|---|---|---|---|---|---|
| | Added Amount of Titanium Oxide Particles (Parts by mass) | Added amount of MEK (Parts by mass) | Added amount of Surfactant (Parts by Mass) | Concentration of Titanium Oxide Particles (% by Mass) | Added Amount of Cuprous Oxide Particles (Parts by Mass) | Added amount of MEK (Parts by mass) | Added amount of Surfactant (Parts by Mass) | Concentration of Cuprous Oxide Particles (% by Mass) | | | |
| Example 1 | 100 | 800 | 10 | 11 | 100 | 2500 | 50 | 4 | 455 | 27 | 245 |
| Example 2 | 100 | 1800 | 10 | 5 | 100 | 2500 | 50 | 4 | 955 | 27 | 245 |
| Example 3 | 100 | 300 | 10 | 24 | 100 | 2500 | 50 | 4 | 205 | 27 | 245 |
| Example 4 | 100 | 800 | 10 | 11 | 100 | 10000 | 50 | 1 | 455 | 102 | 245 |
| Example 5 | 100 | 800 | 10 | 11 | 100 | 800 | 50 | 11 | 455 | 10 | 245 |
| Example 6 | 100 | 800 | 25 | 11 | 100 | 2500 | 50 | 4 | 453 | 27 | 245 |
| Example 7 | 100 | 800 | 5 | 11 | 100 | 2500 | 50 | 4 | 453 | 27 | 245 |
| Example 8 | 100 | 800 | 10 | 11 | 100 | 2500 | 70 | 4 | 455 | 27 | 245 |
| Example 9 | 100 | 800 | 10 | 11 | 100 | 2500 | 20 | 4 | 455 | 26 | 245 |
| Example 10 | 100 | 800 | 10 | 11 | 100 | 2500 | 50 | 4 | 182 | 27 | 245 |
| Example 11 | 100 | 800 | 10 | 11 | 100 | 2500 | 50 | 4 | 819 | 27 | 45 |
| Example 12 | 100 | 800 | 10 | 11 | 100 | 2500 | 50 | 4 | 455 | 13 | 248 |
| Example 13 | 100 | 800 | 10 | 11 | 100 | 2500 | 50 | 4 | 455 | 212 | 210 |
| Example 14 | 100 | 800 | 10 | 11 | 100 | 2500 | 50 | 4 | 455 | 27 | 245 |
| Example 15 | 100 | 800 | 10 | 11 | 100 | 2500 | 50 | 4 | 455 | 27 | 245 |

TABLE 2

|  | Titanium Oxide Particle Dispersion Liquid | | | | Cuprous Oxide Particle Dispersion Liquid | | | | Mixed Amount of Titanium Oxide Particle Dispersion Liquid (Parts by Mass) | Mixed Amount of Cuprous Oxide Particle Dispersion Liquid (Parts by Mass) | Mixed Amount of Binder Resin (Parts by Mass) |
|---|---|---|---|---|---|---|---|---|---|---|---|
|  | Added Amount of Titanium Oxide Particles (Parts by mass) | Added amount of MEK (Parts by mass) | Added amount of Surfactant (Parts by Mass) | Concentration of Titanium Oxide Particles (% by Mass) | Added Amount of Cuprous Oxide Particles (Parts by Mass) | Added amount of MEK (Parts by mass) | Added amount of Surfactant (Parts by Mass) | Concentration of Cuprous Oxide Particles (% by Mass) | | | |
| Comparative Example 1 | 100 | 2500 | 10 | 4 | 100 | 2500 | 50 | 4 | 1305 | 27 | 245 |
| Comparative Example 2 | 100 | 800 | 100 | — | — | — | — | — | — | — | — |
| Comparative Example 3 | 100 | 800 | 10 | 11 | 100 | 15000 | 50 | 1 | 455 | 152 | 245 |
| Comparative Example 4 | — | — | — | — | 100 | 100 | 50 | — | — | — | — |
| Comparative Example 5 | 100 | 800 | 50 | 11 | 100 | 2500 | 50 | 4 | 475 | 27 | 245 |
| Comparative Example 6 | 100 | 800 | 0.5 | — | — | — | — | — | — | — | — |
| Comparative Example 7 | 100 | 800 | 10 | 11 | 100 | 2500 | 200 | 4 | 455 | 28 | 245 |
| Comparative Example 8 | — | — | — | — | 100 | 2500 | 5 | — | — | — | — |
| Comparative Example 9 | — | — | — | — | 100 | 2500 | 50 | 4 | 0 | 27 | 495 |
| Comparative Example 10 | 100 | 800 | 10 | 11 | 100 | 2500 | 50 | 4 | 865 | 27 | 20 |
| Comparative Example 11 | 100 | 800 | 10 | 11 | — | — | — | — | 455 | 0 | 250 |
| Comparative Example 12 | 100 | 800 | 10 | 11 | 100 | 2500 | 50 | 4 | 455 | 530 | 250 |
| Comparative Example 13 | 100 | 800 | 10 | 11 | 100 | 2500 | 50 | 4 | 455 | 27 | 245 |

The titanium oxide particle dispersion liquids, cuprous oxide particle dispersion liquids, and coating agent compositions obtained in the examples and comparative examples described above are subjected to the following evaluation tests. The results of the evaluation tests are shown in Tables 3 and 4.

[Dispersion Property]

Evaluation was conducted to determine whether the processed liquid after the pre-dispersion treatment by use of the stirrer could be transferred to the dispersing apparatus from the stirrer via a fluid transfer pump so as to be subjected to the main dispersion treatment by use of the dispersing apparatus. The examples in which the processed liquid could be transferred to the dispersing apparatus are indicated by "○", and the examples in which the processed liquid could not be transferred to the dispersing apparatus because of excessively high viscosity of the processed liquid are indicated by "x". Here, the fluid transfer pump used was a Masterflex fluid transfer pump (manufactured by Masterflex) including a PTFE pump head.

[Average Secondary Particle Diameter]

The average secondary particle diameters of titanium oxide particles and cuprous oxide particles are measured by dynamic light scattering using cumulant analysis for the titanium oxide particle dispersion liquid and cuprous oxide particle dispersion liquid obtained in each example. The particle diameters are measured by using a concentrated system particle size analyzer FPAR-1000 (manufactured by Otsuka Electronics Co., Ltd.).

[Transparency]

The titanium oxide particle dispersion liquid obtained in each example is adjusted using methyl ethyl ketone so that the concentration of titanium oxide is 1% by mass. Next, the diluted titanium oxide particle dispersion liquid is applied onto a glass plate using a bar coater #10. The obtained applied coating is dried at 50° C. for 30 minutes. After drying, the obtained thin film is measured in terms of haze with a haze meter NDH 4000 (manufactured by Nippon Denshoku Industries Co., Ltd.). The examples having haze values of not more than 3 are evaluated as "○", and the examples having haze values of not less than 3 are evaluated as "x". The transparency of the cuprous oxide particle dispersion liquid is evaluated in the same manner.

[Antibacterial Performance]

The antibacterial performance is evaluated using *Escherichia coli* according to JIS R1702 (Fine ceramics (advanced ceramics, advanced technical ceramics)-Test method for antibacterial activity of photocatalytic products and efficacy). The light irradiation is performed under the following conditions: irradiation by fluorescent light of 1000 Lx (total luminous flux) for one hour. The examples in which the antibacterial activity value per one hour is not less than 3 are evaluated as "○", the examples in which the antibacterial activity is not less than 0.5 and less than 3 are evaluated as "Δ", and the examples in which antibacterial activity is less than 0.5 are evaluated as "x".

[Antiviral Performance]

The antiviral performance are evaluated according to JIS R1756 (Fine ceramics (advanced ceramics, advanced technical ceramics)—Determination of antiviralactivity of photocatalytic materials under indoor lighting environment-Test method using bacteriophage Q-beta), which is set as an alternate evaluation method for the antiviral activity test. Light irradiation is performed in the following conditions: irradiation by fluorescent light of 1000 Lx (total luminous flux) for one hour. The examples in which the antibacterial activity value per one hour is not less than 3 are evaluated as "○", the examples in which the antibacterial activity is not less than 0.5 and less than 3 are evaluated as "Δ", and the examples in which the antibacterial activity is less than 0.5 are evaluated as "x".

[Film Formation Performance]

The coating agent compositions of Examples 1 to 14 and Comparative Examples 1 to 13 are applied onto glass plates (10 cm wide, 10 cm long, and 2 mm thick) using a bar coater #10 and then are dried at 100° C. for 30 seconds, thus preparing a coating film of each example. The obtained coating film of Example 14 is further subjected to ultraviolet irradiation at 800 mJ/cm$^2$ using an ultraviolet irradiator for curing.

Moreover, the coating agent composition of Example 15 is applied onto a polypropylene substrate using a bar coater #10 and is then dried at 80° C. for three hours, thus preparing a coating film of Example 15. The polypropylene substrate is PP1300 PP plate (polypropylene)/press natural (trade name) by Takiron Co., Ltd.

Thereafter, the coating film obtained in each example was touched with a finger to evaluate a dried condition thereof. In particular, the middle of the coating film in each example was touched with a finger. The examples in which no fingerprint could be visually recognized are indicated by "○", and the examples in which a fingerprint was visually recognized are indicated by "x".

[Adhesion Performance (Sticking Performance)]

Evaluation of adhesion performance was conducted on the coating film obtained in the evaluation of the film formation performance in each of examples and comparative examples at a cut interval of 1 mm in accordance with a cross-cut method prescribed in JIS K5600 (Testing methods for paints). The examples in which no abrasion was confirmed are indicated by "○", the examples in which some abrasion was confirmed are indicated by "x".

[Pencil Hardness]

The coating films of the examples and comparative examples obtained in the film formation performance evaluation are evaluated according to Scratch hardness test (Pencil method) of JIS K5600 (Testing methods for paints).

[Scratch Resistance]

The coating films of the examples and comparative examples obtained in the film formation performance evaluation are rubbed with steel wool (Grade: #0000) 50 strokes with a load of 100 g/cm$^2$. It is then examined whether any abrasion is observed in the surface of the coating film. The examples in which no abrasion is visually confirmed are evaluated as "○", and the examples in which abrasion is visually confirmed are evaluated as "x".

[Contact Angle]

The static contact angle is measured in 5 seconds after 0.3 mg of oleic acid is dropped onto the coating film of each example or comparative example obtained in the film formation performance evaluation. The static contact angle is measured using a contact angle meter (CA-DT by Kyowa Interface Science Co., Ltd.).

TABLE 3

| | Titanium Oxide | | Cuprous Oxide | | | | | | | | | |
|---|---|---|---|---|---|---|---|---|---|---|---|---|
| | Dispersion Property | Average Secondary Particle Diameter (nm) | Dispersion Property | Average Secondary Particle Diameter (nm) | Transparency | Antibacterial Performance | Antiviral Performance | Film Formation Performance | Adhesion Performance | Pencil Hardness | Scratch Resistance | Contact Angle of oleic acid (°) |
| Example 1 | ○ | 93 | ○ | 102 | ○ | ○ | ○ | ○ | ○ | HB | ○ | 30 |
| Example 2 | ○ | 90 | ○ | 102 | ○ | ○ | ○ | ○ | ○ | HB | ○ | 30 |
| Example 3 | ○ | 100 | ○ | 102 | ○ | ○ | ○ | ○ | ○ | HB | ○ | 32 |
| Example 4 | ○ | 93 | ○ | 97 | ○ | ○ | ○ | ○ | ○ | HB | ○ | 27 |
| Example 5 | ○ | 93 | ○ | 120 | ○ | ○ | ○ | ○ | ○ | HB | ○ | 32 |
| Example 6 | ○ | 92 | ○ | 102 | ○ | ○ | ○ | ○ | ○ | HB | ○ | 30 |
| Example 7 | ○ | 95 | ○ | 102 | ○ | ○ | ○ | ○ | ○ | HB | ○ | 30 |
| Example 8 | ○ | 93 | ○ | 100 | ○ | ○ | ○ | ○ | ○ | HB | ○ | 30 |
| Example 9 | ○ | 93 | ○ | 110 | ○ | ○ | ○ | ○ | ○ | HB | ○ | 30 |
| Example 10 | ○ | 93 | ○ | 102 | ○ | ○ | ○ | ○ | ○ | HB | ○ | 30 |
| Example 11 | ○ | 93 | ○ | 102 | ○ | ○ | ○ | ○ | ○ | HB | ○ | 30 |
| Example 12 | ○ | 93 | ○ | 102 | ○ | ○ | ○ | ○ | ○ | HB | ○ | 30 |
| Example 13 | ○ | 93 | ○ | 102 | ○ | ○ | ○ | ○ | ○ | HB | ○ | 30 |
| Example 14 | ○ | 93 | ○ | 102 | ○ | ○ | ○ | ○ | ○ | HB | ○ | 10 |
| Example 15 | ○ | 93 | ○ | 102 | ○ | ○ | ○ | ○ | ○ | HB | ○ | 30 |

TABLE 4

| | Titanium Oxide | | Cuprous Oxide | | | | | | | | | |
|---|---|---|---|---|---|---|---|---|---|---|---|---|
| | Dispersion Property | Average Secondary Particle Diameter (nm) | Dispersion Property | Average Secondary Particle Diameter (nm) | Transparency | Antibacterial Performance | Antiviral Performance | Film Formation Performance | Adhesion Performance | Pencil Hardness | Scratch Resistance | Contact Angle of oleic acid (°) |
| Comparative Example 1 | ○ | 95 | ○ | 102 | ○ | ○ | ○ | x | ○ | B | x | 30 |
| Comparative Example 2 | x | — | — | — | — | — | — | — | — | — | — | 30 |
| Comparative Example 3 | ○ | 93 | ○ | 96 | ○ | ○ | ○ | x | ○ | B | x | 32 |
| Comparative Example 4 | — | — | x | — | — | — | — | — | — | — | — | 35 |

TABLE 4-continued

| | Titanium Oxide | | Cuprous Oxide | | | | | | | | | |
|---|---|---|---|---|---|---|---|---|---|---|---|---|
| | Dispersion Property | Average Secondary Particle Diameter (nm) | Dispersion Property | Average Secondary Particle Diameter (nm) | Transparency | Antibacterial Performance | Antiviral Performance | Film Formation Performance | Adhesion Performance | Pencil Hardness | Scratch Resistance | Contact Angle of oleic acid (°) |
| Comparative Example 5 | ○ | 93 | ○ | 102 | ○ | ○ | ○ | ○ | ○ | B | x | 26 |
| Comparative Example 6 | x | — | — | — | — | — | — | — | — | — | — | 28 |
| Comparative Example 7 | ○ | 93 | ○ | 90 | ○ | x | x | ○ | ○ | HB | x | 30 |
| Comparative Example 8 | — | — | x | — | — | — | — | — | — | — | — | 30 |
| Comparative Example 9 | — | — | ○ | 102 | ○ | x | x | ○ | ○ | HB | ○ | 30 |
| Comparative Example 10 | ○ | 93 | ○ | 102 | ○ | x | x | ○ | ○ | HB | ○ | 30 |
| Comparative Example 11 | ○ | 93 | — | — | ○ | x | x | ○ | ○ | HB | ○ | 30 |
| Comparative Example 12 | ○ | 93 | ○ | 102 | ○ | ○ | ○ | ○ | ○ | B | x | 30 |
| Comparative Example 13 | ○ | 93 | ○ | 102 | ○ | x | x | ○ | ○ | HB | ○ | 30 |

As shown in Table 3, the copper complex titanium oxide dispersion liquids of Examples 1 to 15 have good results in the dispersion property evaluation, and the coating agent compositions obtained have good results in each evaluation of transparency, antibacterial performance, antiviral performance, film formation performance, adhesion performance, pencil hardness, and scratch resistance. In Example 14, the contact angle of oleic acid is 10 degrees, showing good results in fingerprint resistance. Moreover, Example 15 has good adhesion to the less-adhesive substrate such as polypropylene.

On the other hand, as shown in Table 4, in Comparative Examples 1 and 3 each including an excessive amount of the organic solvent, the coating properties such as film formation performance, pencil hardness, and scratch resistance are poor. In Comparative Example 2, which includes an excessive amount of surfactant, and Comparative Example 6, which includes an insufficient amount of surfactant, the processed liquid has high viscosity, and the titanium oxide particle dispersion liquid cannot be prepared. In Comparative Example 4, which includes an insufficient amount of organic solvent, the processed liquid has high viscosity, and the cuprous oxide particle dispersion liquid cannot be prepared. In Comparative Example 7, which includes an excessive amount of surfactant, the coating film has low scratch resistance and thereby has low antibacterial and antiviral performances. In Comparative Example 8, which includes an insufficient amount of surfactant, the obtained processed liquid has high viscosity, and the cuprous oxide particle dispersion liquid cannot be prepared.

Comparative Example 9, which does not include titanium oxide particles, and Comparative Example 11, which does not include cuprous oxide particles, produce inadequate results in terms of the antibacterial and antiviral performances. Comparative Example 10, which includes an insufficient amount of cuprous oxide particles, produces inadequate results in terms of the antibacterial and antiviral performances. Comparative Example 12, which includes an excessive amount of cuprous oxide particles, has poor coating properties including pencil hardness and scratch resistance. Comparative Example 13, which employs a surfactant different from the phosphate ester-based anionic surfactant, results in high dispersion of particles but low antibacterial and antiviral performances.

The entire contents of Japanese Patent Application No. 2013-050239 (filed on Mar. 13, 2013), No. 2013-094288 (filed on Apr. 26, 2013), and No. 2013-257283 (filed on Dec. 12, 2013) are incorporated herein by reference.

Although the present invention has been described above by reference to the examples, the present invention is not limited to the descriptions thereof, and it will be apparent to those skilled in the art that various modifications and improvements can be made.

INDUSTRIAL APPLICABILITY

The copper complex titanium oxide dispersion liquid of the present invention can maintain high dispersion of the titanium oxide particles and the cuprous oxide particles even if the concentrations thereof are increased. Accordingly, it is possible to increase the transparency of the coating agent composition including these particles and the antibacterial/antiviral member including the coating agent composition. Moreover, including not only titanium oxide particles but also cuprous oxide particles and the coating agent composition, the antibacterial/antiviral member exerts high antibacterial and antiviral performances.

The invention claimed is:

1. A copper complex titanium oxide dispersion liquid, comprising:
   titanium oxide particles;
   0.1 to 20 parts by mass of cuprous oxide particles per 100 parts by mass of the titanium oxide particles;
   5 to 100 parts by mass of a phosphate ester-based anionic surfactant per 100 parts by mass of the titanium oxide particles and the cuprous oxide particles combined; and
   300 to 2000 parts by mass of an organic solvent per 100 parts by mass of the titanium oxide particles and the cuprous oxide particles combined,
   wherein the titanium oxide particles and the cuprous oxide particles have an average primary particle diameter of 2 nm to 80 nm and have an average secondary particle diameter of 50 nm to 150 nm, the average secondary particle diameter being measured by dynamic light scattering using cumulant analysis.

2. A coating agent composition, comprising:
the copper complex titanium oxide dispersion liquid according to claim 1; and
a binder resin,
wherein 10 to 80 parts by mass of the titanium oxide particles are contained in 100 parts by mass of non-volatile matter content of the coating agent composition.

3. The coating agent composition according to claim 2, wherein the binder resin contains chlorinated polyolefin.

4. An antibacterial/antiviral member, comprising:
a substrate; and
a coating film which is provided on the substrate and includes the coating agent composition according to claim 2.

5. The antibacterial/antiviral member according to claim 4, wherein the coating film has a static contact angle of 30 degrees or less for oleic acid.

* * * * *